US010874791B2

United States Patent
Mager et al.

(10) Patent No.: US 10,874,791 B2
(45) Date of Patent: Dec. 29, 2020

(54) MEDICAL FLUID BAG RACK AND METHOD TO MANUFACTURE IT, MEDICAL WEIGHING DEVICE AND BLOOD TREATMENT APPARATUS

(71) Applicant: Fresenius Medical Care Deutschland GmbH

(72) Inventors: Gerhard Mager, Bad Homburg (DE); Stefan Oesterreich, Neu-Anspach (DE); Udo Waeber, Offenbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 15/780,311

(22) PCT Filed: Nov. 29, 2016

(86) PCT No.: PCT/EP2016/079097
§ 371 (c)(1),
(2) Date: May 31, 2018

(87) PCT Pub. No.: WO2017/093235
PCT Pub. Date: Jun. 8, 2017

(65) Prior Publication Data
US 2018/0353677 A1 Dec. 13, 2018

(30) Foreign Application Priority Data
Dec. 3, 2015 (DE) .......................... 10 2015 121 065
Feb. 12, 2016 (DE) .......................... 10 2016 102 498

(51) Int. Cl.
*A61M 5/14* (2006.01)

(52) U.S. Cl.
CPC .................................. *A61M 5/1415* (2013.01)

(58) Field of Classification Search
CPC ... A61M 5/1415; A61M 5/1417; B65B 67/12; B65B 67/1238; B65B 67/1255;
(Continued)

(56) References Cited

U.S. PATENT DOCUMENTS 1,694,079 A * 12/1928 Nicholas ............. B65B 67/1255
248/97
2,683,009 A * 7/1954 Owens ................ B65B 67/1205
248/97

(Continued)

FOREIGN PATENT DOCUMENTS

CN 203842105 9/2014
DE 8908071 9/1989
(Continued)

OTHER PUBLICATIONS

International Search Report and Written Opinion in Application No. PCT/EP2016/079097, dated Feb. 14, 2017, 9 pages (English Translation).

(Continued)

*Primary Examiner* — Anita M King
(74) *Attorney, Agent, or Firm* — Fish & Richardson P.C.

(57) ABSTRACT

A medical fluid bag rack for hanging bags containing medical fluid that includes at least one base section; at least two support arms which extend from the base section; and at least one bag rack arm. The at least one bag rack arm extends from the base section or from one of the support arms. Also disclosed are methods for manufacturing the fluid bag rack and devices.

14 Claims, 6 Drawing Sheets

(58) Field of Classification Search
CPC ........ B65F 1/141; B65F 1/1415; B65D 33/02; B65D 33/30
See application file for complete search history.

(56) References Cited

U.S. PATENT DOCUMENTS

| | | | |
|---|---|---|---|
| 2,759,695 A * | 8/1956 | Berner | B65F 1/068 248/95 |
| 3,140,070 A * | 7/1964 | Doebele | B65B 67/1227 248/97 |
| 4,874,141 A * | 10/1989 | Schulz | B65B 67/1255 248/97 |
| 5,803,299 A * | 9/1998 | Sealy, Jr. | B65F 1/062 220/495.07 |
| 5,820,086 A * | 10/1998 | Hoffman | A61M 5/1415 248/125.2 |
| D720,110 S * | 12/2014 | Baisden | B65B 67/1255 D34/5 |
| 10,046,108 B2 * | 8/2018 | Nesler | A61M 5/1415 |
| 10,435,237 B1 * | 10/2019 | Schmeck | B65B 67/1222 |
| 2009/0312694 A1 | 12/2009 | Bedingfield et al. | |
| 2013/0168526 A1 | 7/2013 | Walther et al. | |

FOREIGN PATENT DOCUMENTS

| | | |
|---|---|---|
| DE | 69119897 | 1/1997 |
| DE | 29902375 | 4/1999 |
| DE | 20018130 | 1/2001 |
| DE | 69530482 | 10/2003 |
| DE | 102013000454 | 7/2014 |
| JP | H02-182262 | 10/1995 |

OTHER PUBLICATIONS

International Preliminary Report on Patentability in Application No. PCT/EP2016/079097, dated Jun. 5, 2018, 7 pages (English Translation).

* cited by examiner

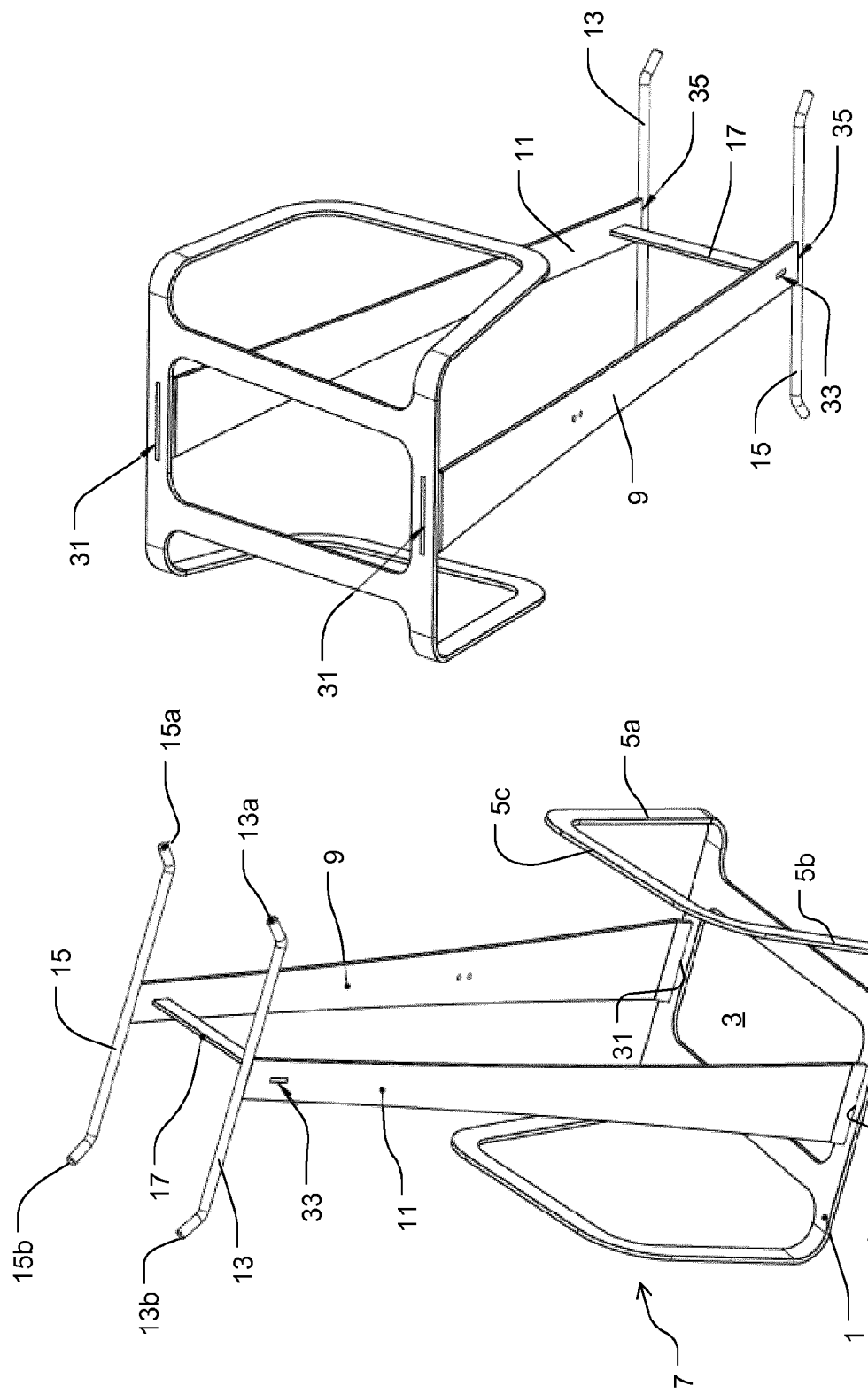

MEDICAL FLUID BAG RACK AND METHOD TO MANUFACTURE IT, MEDICAL WEIGHING DEVICE AND BLOOD TREATMENT APPARATUS

CROSS-REFERENCE TO RELATED APPLICATIONS

The present application is a national stage entry of International Patent Application No. PCT/EP2016/079097, filed on Nov. 29, 2016, which claims priority to Application No. DE 10 2015 121 065.7, filed in the Federal Republic of Germany on Dec. 3, 2015 and Application No. DE 10 2016 102 498.8, filed in the Federal Republic of Germany on Feb. 12, 2016. The disclosures of the prior applications are expressly incorporated herein in entirety by reference thereto.

TECHNICAL FIELD

This disclosure relates to apparatuses for holding medical containers. The disclosure further relates to methods of manufacturing the apparatuses.

BACKGROUND

Fluid bag racks hold bags containing medical fluid for use during various medical activities. Bag racks can typically hold one or more fluid bags and can be used to transport fluid bags.

SUMMARY

Medical fluid bag racks for hanging bags containing medical fluid thereon are described herein. The fluid bag rack includes at least one base section. It further includes at least two support arms which extend directly or indirectly, respectively, from at least one base section, or from one or more base sections in case there are several base sections, from one common base section in case there are several base sections or from different base sections. Finally, it includes at least a bag rack arm, which extends—directly or indirectly—from at least one base section or from one of the support arms.

This disclosure also describes methods for manufacturing a fluid bag rack, or for manufacturing a base body thereof including one base section, two support arms and at least one bag rack arm with or without hooks. The method includes:
 punching or laser-cutting of one, two or several metal strips or blanks for manufacturing a base section, at least two support arms, which extend from the base section—directly or indirectly—and at least a bag rack arm, wherein base section, support arms and bag rack arms are comprised by one or two metal strips;
 bending and/or canting, edging or creasing one or several metal strips and;
 connecting the one metal strip to itself or connecting the two or several metal strips to each other such that a closed or circumferential structure is formed.

Some embodiments relate further to a medical weighing device having at least one fluid bag rack, one weighing unit, and one scale preferably connected thereto in a detachable manner.

The scale includes at least one side surface or another section with a protrusion facing towards the interior or center of the scale. The protrusion serves the positive or form-fit, detachable connection between scale and support arm, in that the protrusion is preferably being received in the slot or the through opening of the support arm of the fluid bag rack.

Finally, some embodiments described herein relate to a medical treatment apparatus which includes at least a fluid bag rack or at least a weighing device.

In the following, the use of the expression "may be" or "may have" and so on, is to be understood synonymously with "preferably is" or "preferably has," respectively, and so on, and is intended to illustrate an embodiment.

Embodiments may comprise one or more of the previous or following features.

Whenever numerical words are mentioned herein, the person skilled in the art understands this as an indication of a numerical lower limit. Unless it leads the skilled person to an evident contradiction, the skilled person implicitly understands when specifying for example "one" always as "at least one". This understanding is also encompassed in certain aspects, as the interpretation that a numeric word, for example, "one" may alternatively mean "exactly one", wherever this is not evidently technically impossible for the skilled person. Both are encompassed in certain aspects and apply herein to all used numerical words.

The indications "top" and "bottom" are to be understood herein—in case of doubt on the part of the skilled person—as absolute or relative spatial indications which refer to the arrangement of the relevant component while in use as intended and/or to the representation in the accompanying figures.

Certain aspects refer to any arbitrary combination of the features mentioned herein, provided a concrete combination be not obviously technically impossible for the skilled person.

In specific exemplary embodiments, the base section and the at least two support arms are one-piece or integral. They are preferably manufactured from a common or joint first material strip, in a particular metal strip, thus, saving manufacturing steps.

In some exemplary embodiments, the base section and the at least one bag rack arm are manufactured as one-piece or integrally, preferably from a common or joint, first material strip, in particular a metal strip.

In certain exemplary embodiments, at least one of the support arms and the at least one bag rack arm are manufactured as one-piece or integrally, preferably from one common or joint, first material strip, in particular a metal strip.

In some exemplary embodiments, the fluid bag rack includes a or exactly one bag rack arm which has a cylindrical cross section, is a pillar or has a pillar section and/or is directly or indirectly connected to the base section, preferably to a middle section thereof.

In certain exemplary embodiments, the fluid bag rack includes at least two bag rack arms, which are connected to the base section, respectively, at or on sides of said base section lying opposite to each other, in particular cross sides, or extend or originate as one-piece or integrally therefrom.

In specific exemplary embodiments, two of the support arms are connected to the base section at sides of the base section lying opposite to each other, respectively, or extend as one-piece or integrally from said base section.

In some exemplary embodiments, the fluid bag rack includes at least two bag rack arms which are connected to the base sections at sides of the base section lying opposite to each other, respectively, or extend as one-piece or integrally from said base section. In specific exemplary embodiments, these sides are not the sides at which the support arms are connected to the base section.

In specific exemplary embodiments, the fluid bag rack includes at least two bag rack arms which are connected to each other by at least one connection strut or connection section, in particular in an upper end area of the bag rack arms.

In specific exemplary embodiments, the at least one connecting strut is also a material strip, e.g. metal strip, in particular an integral section of the first material strip or metal strip.

In some particular exemplary embodiments, at least one of the support arms includes at least two lateral struts, which are distant from each other by an open slot or an enclosed through opening.

In some exemplary embodiments, the lateral struts are also metal struts or metal strips, preferably sections of the first metal strip.

In specific exemplary embodiments, at least one or two of the lateral struts—e.g. in their longitudinal section—comprise or consist of at least a curved or bent section, a first straight section and a second straight section. The bent section is closer to the base section than the first straight section, which lies between the bent section and the second straight section. The second straight section has a larger radial distance to the base section, or a larger distance to the base section, than the first straight section. This embodiment causes that the lateral strut cants to the outside with a straight part thereof, which serves clamping of the fluid bag rack or also only its positive or form-fit reception in a scale.

In some exemplary embodiments, the lateral struts are at an angle, which is not 90°, relative to the base section or relative to the main extension direction of the bag rack arms.

In specific exemplary embodiments, the lateral struts are canted to the outside.

In certain exemplary embodiments, the base section includes, or is, a flat section, preferably made of metal.

In some exemplary embodiments, the flat section, preferably in a middle section thereof, includes a through opening or a recess or protrusion, for example in the sense of a bulge or warpage.

In specific exemplary embodiments, the first and/or the second metal strip are made of, preferably stainless, (high-grade) steel.

In specific exemplary embodiments, the first material strip and/or the second material strip, which may be made of metal, have a, preferably constant, thickness being preferably between 1 mm and 8 mm, preferably between 2 mm and 5 mm, particularly preferably, between 3 mm to 4 mm.

In some exemplary embodiments, the at least one bag rack arm includes one or several hooks for hanging one or several fluid bags.

The hook(s) is/are optionally one-piece or integral with the respective bag rack arm.

In specific exemplary embodiments, the fluid bag rack includes at least a holder or support for detachably holding fluid tube sections.

In certain exemplary embodiments, the fluid bag rack includes a closed or circumferential structure which is formed by connecting the base section, one or two bag rack arms and optionally one connecting strut to each other. This structure may comprise or consist of the base section, one or all bag rack arm(s) and the optional connecting strut.

In certain exemplary embodiments, the base section serves placing of the fluid bag rack on a ground, in others, it does not.

The base section may define, have or be a placement surface, or may not.

The base section may be a base surface.

The base section may be made of metal.

The base section may be a platform to rest on.

The base section may be a frame structure or may consist thereof.

The base section may have feet.

In some exemplary embodiments, the fluid bag rack is embodied to be able to stand by itself. It can be a fluid bag stand or rack.

In specific exemplary embodiments, the hooks for the bags are made of metal, e.g. from a suitable blank or cut of the corresponding metal strip.

More than four hooks may be provided.

Any reference made to the metal strip shall apply herein also to a piece of metal which has no strip form or which did not have one. Some embodiments may replace "metal strip" with "metal piece".

In certain exemplary embodiments, the metal strips are made of—preferably stained or pickled and/or ground—stainless steel, e.g. V2A or V4A.

In certain exemplary embodiments, the metal strips are to be, or are, welded to each other.

The metal strips are preferably welded by straight welding seams exclusively.

In certain exemplary embodiments, the metal strips are to be, or are, deburred.

In certain exemplary embodiments, the metal strips are to be, or are, polished.

In certain exemplary embodiments, the material is resistant to corrosive media, in particular to medical disinfectants, chlorine-containing or chloric media, etc.

In certain exemplary embodiments, fluid bag rack and scale are coordinated or matched to each other such that, when inserting the fluid bag rack into the scale, the lateral struts of the support arms are arranged on or contact at least one section of the lateral struts at side surfaces or end sides of the protrusion or protrusions of the scale.

In certain exemplary embodiments of the weighing device, the at least one section, in or by which the lateral struts or at least one section thereof come into contact with the side surfaces or end sides of the protrusion, is part of the end section of the lateral struts which faces away from the base section or is farther to the base section.

In certain exemplary embodiments, fluid bag rack and scale are coordinated such that cross struts of the support arms do not abut or rest on upper surfaces or end sides of the protrusion or protrusions of the scale when inserting the fluid bag rack into the scale.

In specific exemplary embodiments, the cross struts of support arms lying opposite to each other are farther apart than other, sections of the lateral struts, e.g. middle sections.

In certain exemplary embodiments, the lateral struts of the one support arm are provided at a first angle to the lateral struts of the other support arm, and the side surfaces of the protrusion or protrusions are provided at a second angle to each other. Thereby, the first angle and the second angle are the same or substantially the same.

In certain exemplary embodiments, fluid bag rack and scale are coordinated or matched to each other such that the cross struts of the support arms stand parallel or substantially parallel to the upper surfaces or end sides of the protrusion or protrusions of the scale when inserting the fluid bag rack into the scale.

In certain exemplary embodiments, the scale includes a base surface, particularly one out of which the side surfaces extend, wherein the base surface includes a length which is longer than the length of the base section or larger than the distance between a base section of a bag rack arm and a base section-near section of a further bag rack arm lying opposite to first said bag rack arm.

In certain exemplary embodiments, the scale includes side surfaces at its longitudinal sides, however not at its cross sides. The interior of the fluid bag rack is thus not limited at all four sides by vertical structures, like side walls or other structures having also vertical extensions.

In certain exemplary embodiments, the protrusion includes at least a dimension or measurement, preferably an exterior dimension, which preferably approximately corresponds to an interior dimension of the slot or the through opening.

In some exemplary embodiments, the medical treatment apparatus includes at least a holding plate to engage with the rear side of the protrusion of the scale of the weighing device.

In specific exemplary embodiments, the medical treatment apparatus is a blood treatment apparatus.

In some exemplary embodiments, the medical treatment apparatus is embodied as acute dialysis apparatus, dialysis apparatus, hemodialysis apparatus, hemofiltration apparatus, apheresis apparatus, plasma treatment or exchange apparatus, TPE (Therapeutic Plasma Exchange) apparatus and/or combinations thereof.

In some exemplary embodiments, the fluid bag rack includes—particularly at the at least one base section—no rolls, in particular no rolls of a rolling carriage as a movable stand for the reception of infusion devices.

In some exemplary embodiments, the fluid bag rack is provided and designed for inserting it into a scale pan, in particular for inserting it into a scale pan in a releasable manner.

In some exemplary embodiments, the fluid bag rack is no movable stand for the reception of infusion devices.

In some exemplary embodiments, the fluid bag rack is not connected to any pressure arrangement or device for emptying a fluid bag, with the arrangement or device being arranged in or at the fluid bag rack.

In some exemplary embodiments, the fluid bag rack includes no alarm device nor is connected to such a device, wherein the alarm device is intended to trigger an alarm signal, when a, for example predetermined, weight of a fluid bag in the fluid bag rack decreases under an alarm value.

Some or all embodiments may encompass one or several of the aforementioned or following advantages.

The fluid bag rack is embodied in some particular embodiments to support itself, with upper sections of the lateral struts of its support arms at side surfaces of the scale of a weighing device. A stable placement of the fluid bag rack in the scale is ensured, as the upper sections due to their lever arm, effectively support themselves against protrusions of the scale and thereby prevent a rotation or a tilting of the fluid bag rack about its wide side or about an axis.

Since the fluid bag rack, as set forth, stands stable in the scale due to its designed tilt-safe mechanism achieved by the upper sections of the lateral struts of the support arms and the protrusions of the side surfaces of the scale, the wide or cross sides of the scale may remain open. "Remain open" is to be understood here such that the cross sides, unlike the longitudinal sides, are not necessarily limited by walls or side surfaces against which the fluid bag rack may be supported in order not to tilt. The open cross sides offer the advantage that fluid bags to be hanged on the bag rack arms may not only be hanged from the top (which may be inconvenient) but also from the sides of the "missing" cross sides-side surfaces (which is more convenient). Furthermore, the "missing" cross sides-side surfaces allow an unhampered view of the hanged or hanging fluid bags and of the liquid contained inside from the side or from a distance also even if there are only remnants of liquid in the fluid bag, and particularly in the bottom area of the fluid bag.

The fluid bag rack according to the present invention may offer, compared to the prior art, further advantages which are based on the fact that the steps required for manufacturing the fluid bag rack may be automated due to the construction of the fluid bag rack.

Therefore, and due to the selection of the material, the fluid bag rack may be manufactured at low cost.

At the same time, the fluid bag rack may have comparatively low weight due to its construction and materials. Its low weight may allow handling it easily and better weighing results, since lower weight allows working in a lower measuring range of the scale.

Further advantages, in particular those of the exemplary embodiments shown in the figures, are explained hereinafter.

BRIEF DESCRIPTION OF THE FIGURES

The present invention shall be exemplarily explained hereinafter with reference to the accompanying drawings in which identical reference numerals refer to same or similar components. The following applies in the partly strongly simplified figures:

FIG. 5 shows a second example embodiment of a fluid bag rack in perspective view;

FIG. 6 shows a second embodiment of the fluid bag rack in perspective view, diagonally from below;

DETAILED DESCRIPTION

Figure 1:
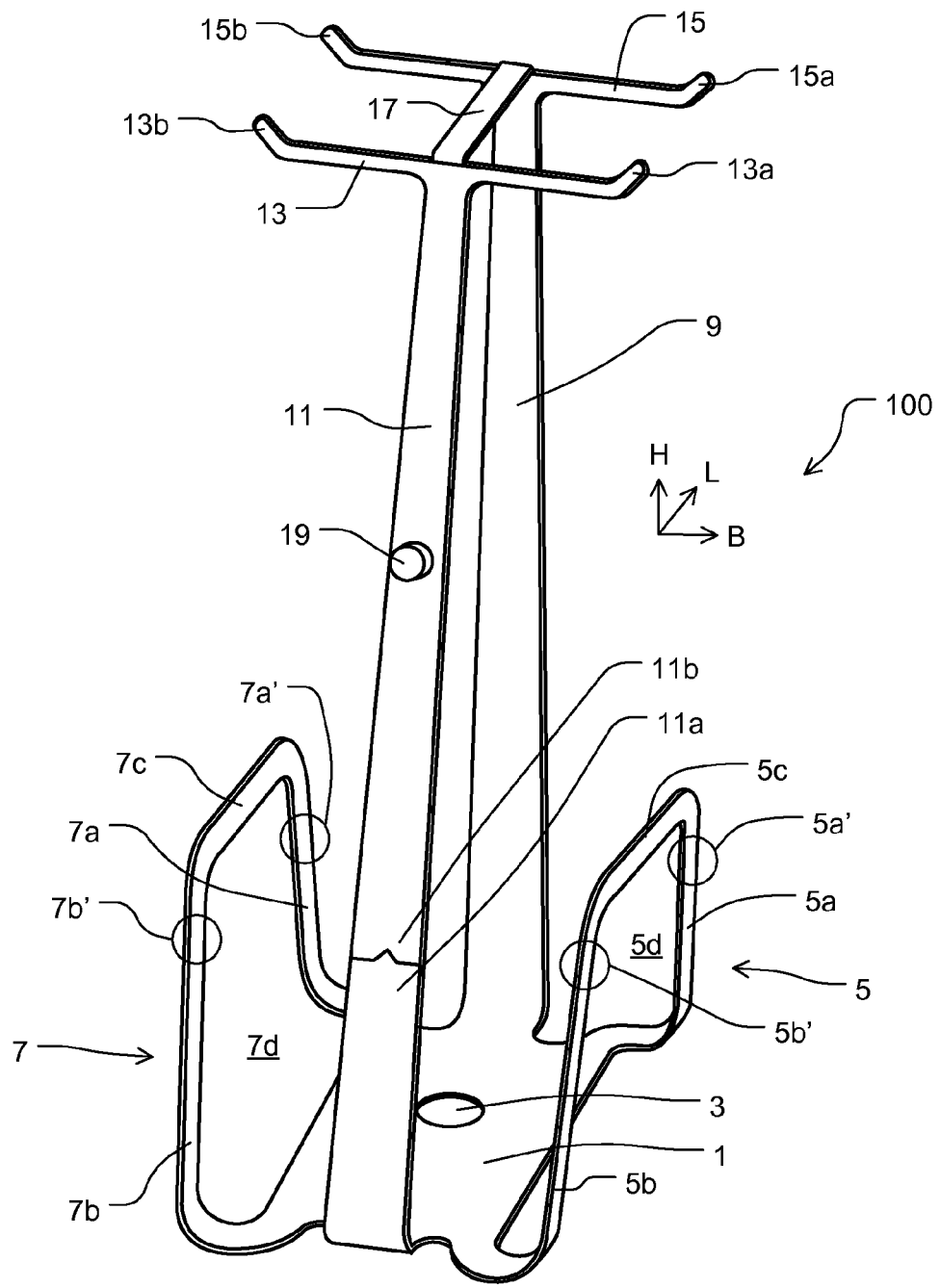
FIG. 1 shows a fluid bag rack in a first example embodiment, in a perspective view.

FIG. 1 shows a first exemplary embodiment of the fluid bag rack 100 in a perspective view.

The fluid bag rack 100 comprises a base section 1 having longitudinal edges or sides and transverse edges or sides and an optional through opening in a central or middle area thereof, which is in short hereinafter referred to as opening 3. The area above the opening 3 is considered herein as an interior or as an inner section of the fluid bag rack 100.

Protruding from the base section, two support arms 5 and 7 elevate or rise upward, which stretch or depart from first or second longitudinal sides of the base section 1 lying opposite to each other.

The support arms 5, 7 comprise each two lateral struts 5a and 5b or 7a and 7b, respectively, which are optionally interconnected to each other by an optional cross strut 5c or 7c, respectively. It is recognizable that there is a slot between two respective lateral struts 5a and 5b or 7a and 7b, respectively, which is an enclosed through space 5d or 7d, respectively, due to the optional cross struts 5c, 7c. Without the optional cross struts 5c, 7c, one would speak of a slot, not however of a through space in the sense of an opening or through opening.

Protruding from base section 1, further two bag rack arms 9, 11 elevate, which serve hanging known or standard fluid bags (not shown in the figures). They also protrude from third or fourth cross sides of the base section 1 lying opposite to each other.

The bag rack arms 9, 11 may comprise hooks 13, 15 for hanging the aforementioned fluid bags. They may extend away, e.g. by a right angle, from the bag rack arms 9, 11 and/or protrude therefrom. They may have the design of arms comprising, relative to the arm, bent peaks 13a, 13b or 15a, 15b, respectively.

The bag rack arms 9, 11 are in FIG. 1 interconnected to each other by an optional connecting strut 17. The connecting strut may be placed in any section of the bag rack arms 9, 11. In the example of FIG. 1, it is placed in the area of the hooks 13, 15, which are interconnected to each other by the connecting strut 17.

In FIG. 1, as well as in the following figures, the bag rack arms 9, 11 are shown as paired and as sections of metal strips. However, there may be only one bag rack arm provided in some embodiments. Furthermore, the one or the two bag rack arms may alternatively be designed as pillars or structures having a round or elliptical cross-section.

As is seen in FIG. 1 the base section 1, the bag rack arms 9, 11 and the connecting strut 17 are connected to form a closed or circumferential structure, which is probably comparable to a frame being narrower at the top than at the bottom.

The closed or circumferential structure is wider in the area of the base section 1 than in the area of the connecting strut 17, which is arranged between the bag rack arm 9 and 11 and connected to both. The connecting strut 17 may be shorter than the base section 1.

Such design contributes to higher stability of the fluid bag rack 100, which in turn advantageously permits to manufacture the latter from a simple metal strip, which is, for example, only bent several times and possibly welded or otherwise connected to itself at one or at few points or places. In the case that the metal strips are welded together, the weld seam may be straight or preferably also even short, due to the strip form of the metal plate. This is again advantageous as the demands for straight weld seams and the manufacturing efforts are little.

At least one of the bag rack arms, presently the bag rack arm 11, comprises, preferably at its exterior side, one or several holdings 19. The latter serves the attaching of sections of fluid tubes in a detachable manner and thus ensures a certain arrangement of the fluid tubes. The holdings 19 may be connected as desired to the bag rack arm (e.g. screwed, welded, as one-piece or integral, glued, etc.).

The bag rack arms 9, 11 are closer to each other at their upper ends or sections than they are at their base or bottom-near sections, e.g. because the length of the base section 1 (in L-direction in FIG. 1) of substantially straight bag rack arms 9,11 is longer than the length of the connecting strut 17. This may advantageously contribute in that the fluid bag rack 100 loaded with fluid bags hanging on the hooks 13, 15 may remain stable despite the weight of the hanging bags.

The holders 19 may have a round diameter. They may be designed for clamping, simple laying or holding up the tubing sections etc. They may be designed as a cylinder having a notch in radial direction which e.g. takes one third or half of the diameter, and into which the tubing sections may be clamped. However, they may also be provided as simple hooks for hanging the tubing sections.

As is seen in FIG. 1 the fluid bag rack 100 of this exemplary embodiment is formed from one or more sheet metals or metal strips, wherein it is enough to use one metal strip and to connect the latter to itself in order to create or form a closed structure, e.g. by means of one single, optionally also even short, welding seam.

Figure 2:
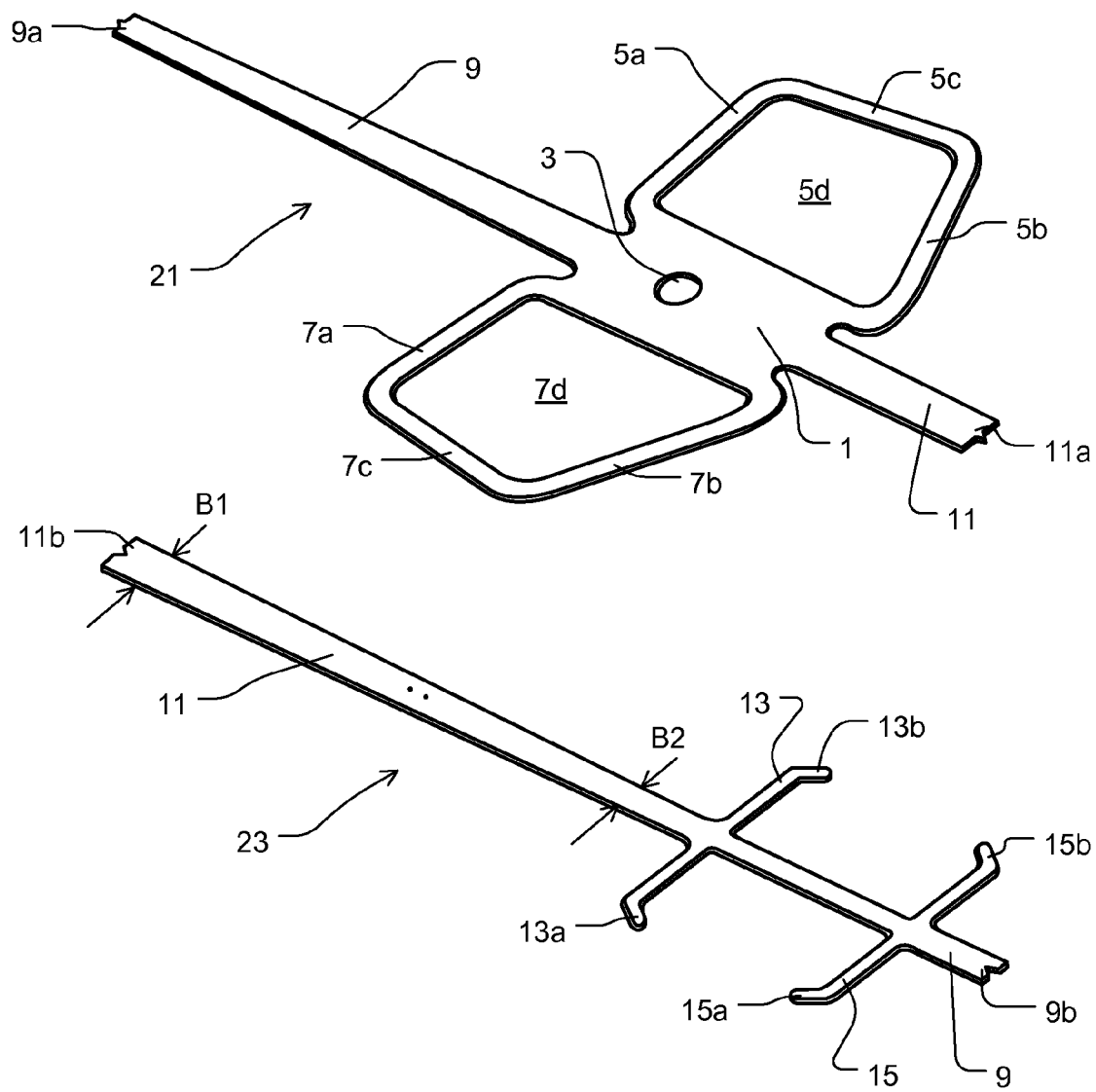
FIG. 2 shows two metal strips from which the fluid bag rack may be manufactured or of which it may consist.

The fluid bag rack 100, may, deviating from this design, of course also be made of two or more metal strips or sections, or comprise the same, which are interconnected to each other with correspondingly more connections. FIG. 2 shows an example in which two metal strips and two connections, herein two, optionally short, welding seams are used.

FIG. 1 further shows abutting or contacting edges or ends 11a, 11b. They are hereinafter explained with respect to FIG. 2.

The lateral struts 5a and 5b or 7a and 7b, respectively, comprise each two end areas, herein referred to as base section-near or base section-far. The end areas referred to with the reference numerals 5a', 5b', 7a' and 7b' are the base sections-far ones, which are those which face away from the base section 1.

The reference system drawn in FIG. 1 indicates the direction of height H, the length L and the width B of the fluid bag rack 100 shown in FIG. 1. This reference system applies also for the following FIG. 2 to FIG. 4 and to all the apparatuses shown therein.

FIG. 2 shows a flat, first metal strip 21 and a flat, second metal strip 23 of which the fluid bag rack 100 of FIG. 1 may be made of or may comprise.

The metal strips 21 and 23 are shown in FIG. 2 after blanking or punching each of them out of metal strip. They are not yet bent and not yet interconnected to each other for achieving the design of the complete fluid bag rack 100.

Sections of bag rack arms 9, 11 are provided, as seen in FIG. 2, partly on the first metal strip 21 and partly on the second metal strip 23, respectively. These sections comprise abutting edges 9a and 9b or 11a and 11b, at which the two metal strips 21 and 23 are being connected after having been bent.

The first metal strip 21 comprises two abutting edges 9a and 11a in its sections of the bag rack arms 9, 11 and ends therewith at its end sides, respectively.

The second metal strip 23 comprises two abutting edges 9b and 11b in its sections of the bag rack arms 9, 11 and ends therewith at its end sides, respectively.

After bending both metal strips 21 and 23 into their forms, seen in FIG. 1, the abutting edge 9a is connected to the abutting edge 9b. e.g., welded. Likewise, the abutting edge 11a is connected to the abutting edge 11b, e.g. welded. The result of the welding can be seen in FIG. 1, wherein, however, the contact between the abutting edge 9a and the abutting edge 9b is not illustrated separately there.

Since the two metals strips 21 and 23 are flat strips, two welding seams, preferably extending over the width of the strip, preferably short and/or straight are enough to interconnect them to each other, making the manufacturing of the fluid bag rack simple and inexpensive.

In the example of FIG. 2, the first metal strip 21 encompasses or consists of both support arms 5, 7, the base section 1 as well as parts of the bag rack arms 9, 11. The second metal strip 23 encompasses or consists of both hooks 13, 15 as well as parts of the bag rack arms 9, 11.

As can be seen in FIG. 1 and FIG. 2, both bag rack arms 9, 11 extend, respectively, towards the hooks 13 or 15, respectively, whereby the width of the respective metal strips 21, 23 diminishes. The decreasing strip width is exemplarily referred to in FIG. 2 with B1 and B2, wherein B1>B2 applies.

Figure 3:
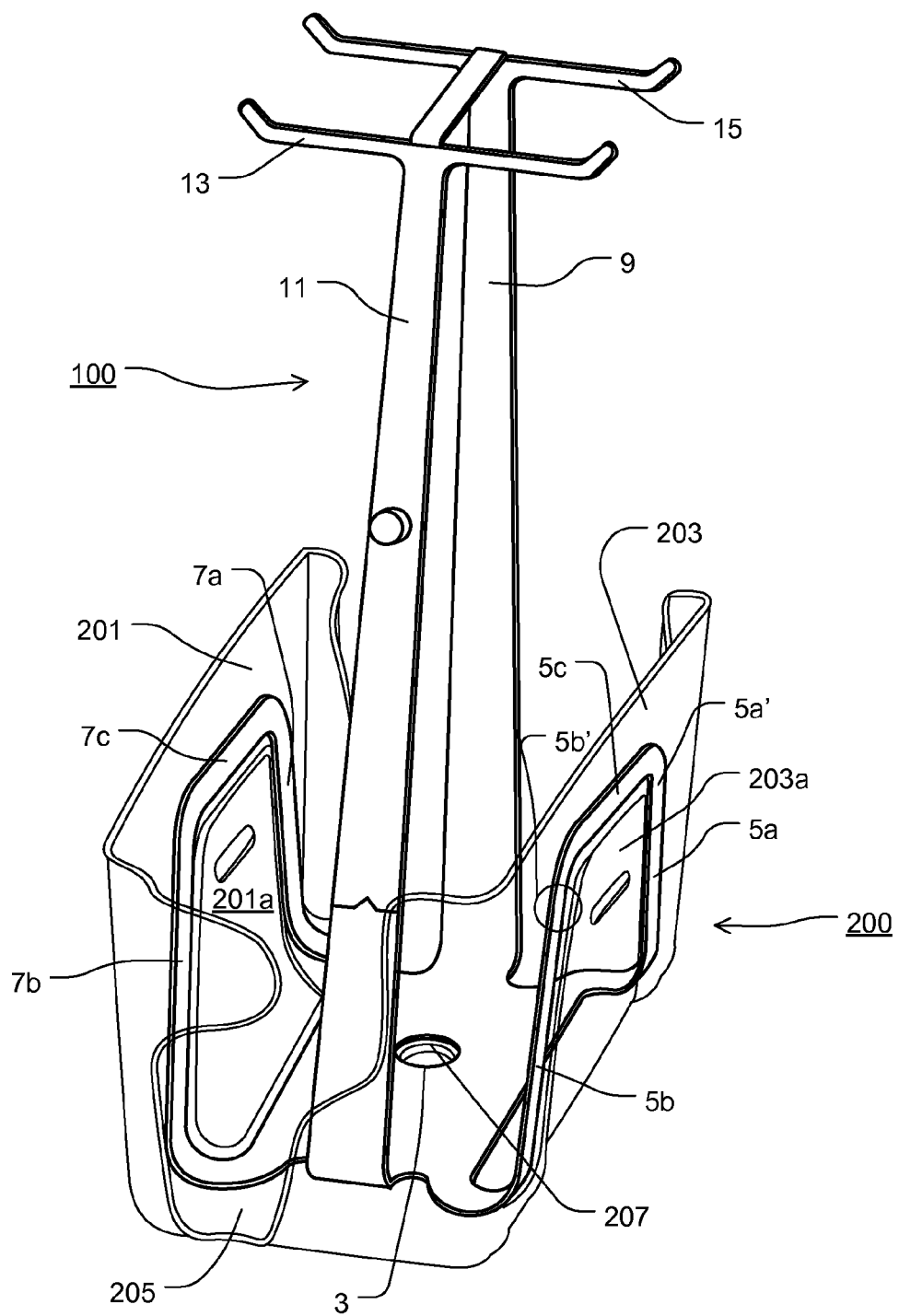
FIG. 3 shows a perspective view of the fluid bag rack of the first embodiment inserted or placed into a scale.

FIG. 3 shows a perspective view of the first embodiment of the fluid bag rack 100, inserted into a scale 200.

The scale 200 is part of a non-illustrated weighing device, which in turn comprises a weighing unit. The weighing unit is set not to display the weight of the fluid bag rack 100 standing or placed in the scale 200. Its weight display is so to speak at zero despite the weight of the fluid bag rack 100. If now a fluid bag is additionally placed in the scale 200, the weighing unit thus displays the weight of the fluid bag. If the fluid bag is alternatively hung on one of the hooks 13, 15, there shall be no change of the displayed weight value; the weighing unit displays again the weight of the fluid bag.

The scale 200 comprises side surfaces 201 and 203 extending upwards in FIG. 3. They extend from a base area 205 and may be one-piece or integral therewith, e.g. as injection-moulded parts.

Both side surfaces 201 and 203 comprise each in a middle or central section thereof, in any case in an interior of the scale 200, in which also the fluid bag rack 100 stands, a protrusion 201a or 203a, respectively. The front sides of the protrusions 201a, 203a protrude against the other side areas 201 and 203. The rear sides of the protrusions 201a, 203a may optionally have a recess, as discussed in FIG. 4.

The protrusions 201a, 203a have a width or form which at least corresponds to the distance or space between the lateral struts 5a, 5b, or 7a, 7b, respectively, or to the form of the slot between the lateral struts 5a, 5b, or 7a, 7b, respectively, or to the form of the through opening between the cross and lateral struts 5c, 5a, 5b, or 7c, 7a, 7b, respectively. In this manner, the support arms 5, 7 may be shifted over one of the protrusions 201a, 203a, respectively, and thus a form closure may be created between slot or through opening 5d, 7d (see FIG. 1) on the one hand, and the protrusion on the other hand. The form closure allows preventing a tilting of the fluid bag rack 100 about the B-axis of FIG. 1, i.e. tilting from the front to the back with respect to the illustration of FIG. 1.

If the lateral struts 5a, 5b, or 7a, 7b, respectively, extend each in an angle towards each other and preferably such that their upper distance is bigger than their lower distance or such that an angle opening further towards the bottom or a trapezoid opening to the bottom is achieved, then this allows on the one hand an advantageous self-centering and adopting a form-closure position by which the lateral struts 5a, 5b, or 7a, 7b, respectively, abut or contact the lateral limitations of the respective protrusion 201a, 203a. On the other hand, this embodiment allows an effortless insertion of the fluid bag rack 100 into the scale 200, by which, advantageously, no jamming of the lateral struts 5a, 5b or 7a, 7b, respectively, on or at the lateral limitations of the respective protrusions 201a, 203a takes place.

The lateral struts 5a, 5b and 7a, 7b are optionally bent in a direction of the width of the fluid bag rack 100 (see the B-direction in FIG. 1), such that they form, starting from the base section 1 or in a section near the base section, another angle relative to the base section 1 than in an upper area, in a section away from the base section or in a tip area of the respective lateral struts 5a, 5b and 7a, 7b. This allows a simple insertion of the fluid bag rack 100 from top to bottom such that a closure or limitation of the through opening 5d, 7d, formed through the base section 1, may be moved past the protrusion 201a, 203a.

Embodiments in which the support arms 5, 7 and the protrusion 201, 203 are coordinated, allows advantageously a stable, tilt-preventing arrangement of the fluid bag rack 100 in the scale 200 under form closure, without requiring a fixing mechanism like e.g. a click mechanism, a snap mechanism, a locking mechanism or the like. As the fluid bag rack 100 can engage in the scale without moving parts, a particularly wear-free and therefore advantageous embodiment is thus provided.

The stability is further increased through the opening 3 already shown in FIG. 1. It is shown in FIG. 3 that the opening 3 receives a gating 207 of the scale 200 which is herein exemplarily manufactured by injection processes or methods. In this manner, the base section 1 does not stand on top of the gating 207; hence, an instable standing of the fluid bag rack 100 due to the gating 207 is prevented.

Thus, the opening 3 allows however also that a possible unevenness of the scale 200, which may result from the (resin or plastic) injection moulding, can be disregarded and that a corresponding postprocessing may be omitted. In this manner, the opening 3 contributes to making the steps of postprocessing become superfluous or unnecessary.

It is seen in FIG. 3 that the protrusion 201a or 203a comprise different widths in parallel cuts perpendicular to the axis H, see FIG. 1. In such cuts, also the inner sides of the lateral struts 5a and 5b or 7a and 7b comprise different distances to each other in the direction L. When the fluid bag rack 100 is inserted into the scale 200, the width of the protrusion 201a and 203a corresponds then, in a cut farther to the base section perpendicular to the axis H, to the distance between the lateral struts 5a and 5b or between 7a and 7b. In other cuts, and above all in cuts nearer to the base section, the width of the protrusion is larger than the distance between the lateral struts; a slot remains there between the lateral struts and the protrusion. Therefore, the weight of the fluid bag rack 100 rests principally also in the aforementioned cutting plane farther to the base section or the section farther to the base section. This contributes to the lever arm effect and to tilt-safety.

Figure 4:
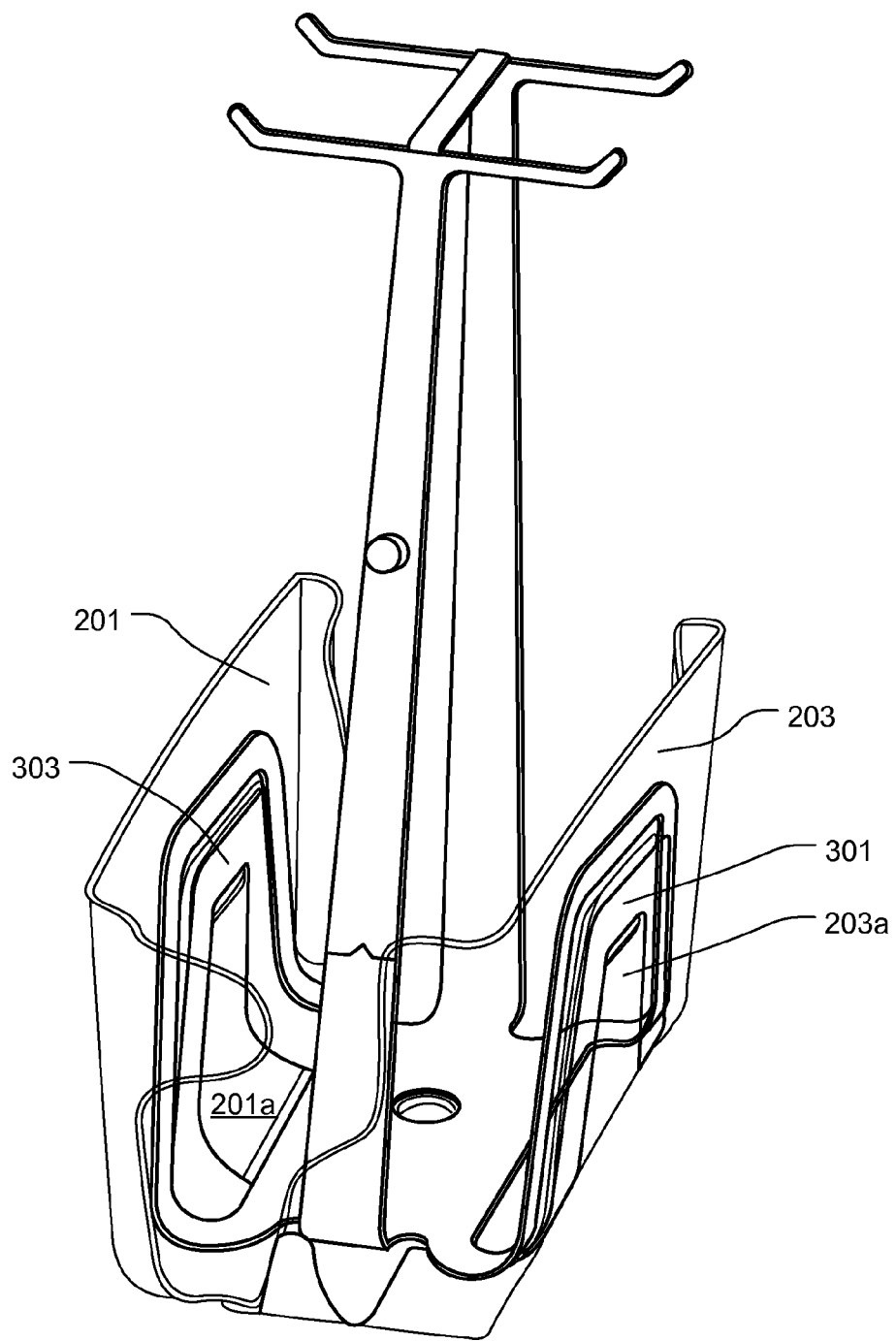
FIG. 4 shows the fluid bag rack of FIG. 3 inserted into the scale of FIG. 3, wherein holding plates of a treatment apparatus engaged further from the outside into the scale are shown.

FIG. 4 shows the fluid bag rack 100 of FIG. 3, inserted into the scale 200 of FIG. 3, wherein holding plates or sheets 301, 303 of a treatment apparatus (not shown in all detail) engaging into the scale 200 are illustrated.

The holding plates 301, 303 engage at a rear side of the side surfaces 201, 203 of the scale 200 into the rear side of the protrusions 201a and 203a, respectively, which are in the exemplary embodiment of FIG. 4 recesses on the rear sides of the side surfaces 201, 203. The holding plates 301, 303, hence, support the scale 200 and prevent it from shifting with regard to the weighing device or the treatment apparatus.

FIG. 5 shows a perspective view of a second exemplary embodiment of the fluid bag rack 100.

The fluid bag rack 100 comprises in its base section 1 an opening 3 being large when compared with the first embodiment. The base section 1 may become a frame structure due to the size of the opening 3, which may contribute to saving weight.

Unlike the first embodiment of FIG. 1, the bag rack arms 9, 11 are optionally one-piece, respectively. They comprise no abutting edges 9a, 9b or 11a, 11b, respectively, by means of which the two metal strips 21 and 23 are interconnected to each other in the first embodiment.

The bag rack arms 9, 11 of the second embodiment shown in FIG. 5 may be exemplarily inserted or slotted in slots or grooves 31 as shown in FIG. 5. The slots or grooves 31 may be open, i.e. open from top to bottom (through openings) through the base section 1; they may alternatively be closed, i.e. extending only through a part of the thickness of the base section 1 (blind hole opening).

The bag rack arms 9, 11 may be inserted, e.g. in a fitting manner, into the slots or grooves 31. They may, additionally or alternatively to the fitting manner, be connected to the base section 1 by other connecting or joining methods, e.g. welded, glued, etc. The slots or grooves 31 may be embodied as welding aid which facilitates a desired arrangement of the bag rack arm 9, 11 onto the base section 1 for the purpose of subsequent welding. The welding may take place from the bottom or from the outside.

Likewise unlike the first embodiments of FIG. 1, the optional connecting strut 17 is not part of the metal strip 21 and 23 or of one of the two bag rack arms 9, 11. It is, in the example of FIG. 5, rather a separate component which is connected to one or, as shown in FIG. 5 to both bag rack arms 9, 11. The connecting strut 17 may be inserted into the slots or grooves 33 of the bag rack arms 9, 11. The slots or grooves 33 may be embodied like the slots or grooves 31. The connection may be carried out as mentioned supra for the connection between bag rack arms 9, 11 and base section 1.

FIG. 6 shows a perspective view of the fluid bag rack 100 of FIG. 5 diagonally from the bottom.

It can be seen that—again unlike in the first embodiment of FIG. 1—the hooks 13, 15 are likewise not part of the metal strips or of one of the two bag rack arms 9, 11. They are rather separate components in the example of FIG. 5 and FIG. 6. They may purely exemplarily be connected to the bag rack arms 9, 11 in a contact area 35 between the hooks 13 and 15 and bag rack arm 9, 11 by means of welding seams. Other connecting methods like gluing etc. are contemplated as well.

Figure 7:
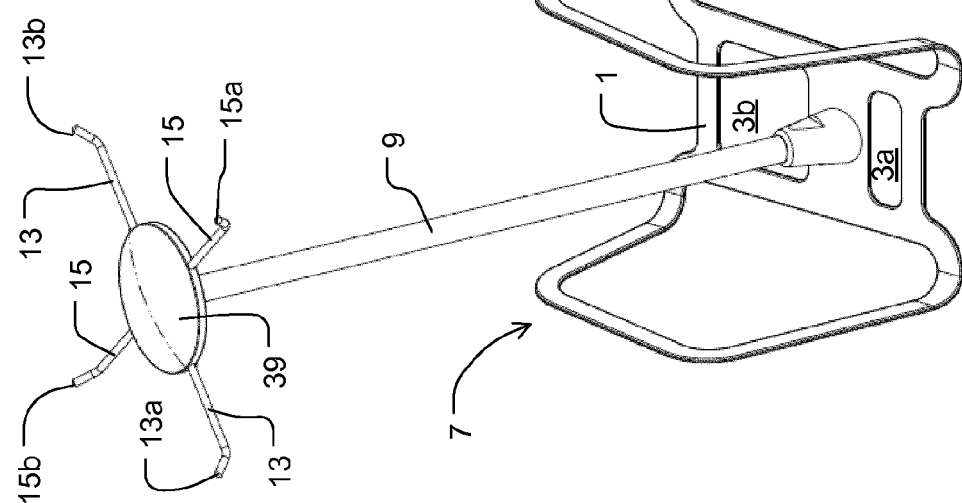
FIG. 7 shows a third example embodiment of a fluid bag rack in perspective view, diagonally from front top.

FIG. 7 shows a perspective view of a third embodiment of the fluid bag rack 100, diagonally from the front and diagonally from above.

Unlike in the first and second embodiments of FIG. 1 to FIG. 6, the fluid bag rack 100 comprises only one bag rack arm 9. The latter, optionally, does not extend one-piece or integrally from the base section 1 or from one of the two metal strips 21 and 23; it is rather connected to the base section 1. In the example of FIG. 7, the bag rack arm 9 is optionally connected to a middle area of the base section 1; other areas of the base section 1 are considered as well. Again, all known connecting methods are applicable; in particular those mentioned herein. The bag rack arm 9 is, purely exemplarily, screwed to the base section 1, with one foot or foot section thereof, by screws 37 (see FIG. 8).

As FIG. 7 shows, the bag rack arm 9 may also be embodied as stick or bar or pillar having for example a round cross section.

The bag rack arm 9 does not, optionally, stand at right angle on the base section 1. An angle between the upper side or the main extension surface of the of the base section 1 and the longitudinal axis or extension of the bag rack arm 9 takes a value between e.g. 65° and 85°, in particular between 70° and 80°. The bag rack arm 9 which does not stand at right angle on the base section 1 advantageously allows to still vertically position and use the bag rack arm 9—preferably substantially or completely—even when the base section 1 itself does not come to rest completely horizontally due to external conditions (which e.g. are attributed to the arrangement and alignment of the scale 200). This advantage is particularly true, when the support arms 5, 7 each may come to lie both right and left in the scale 200; thus, when the fluid bag rack 100 may in this way be inserted—in a twisted manner—in the scale 200 both in a first manner and a second manner which is, relative to the first manner, by 180° about an axis extending in vertical direction. Such twisted manner may be optionally supported or advantaged by a symmetry of the supporting arms 5, 7.

The bag rack arm 9 comprises, at a free or upper end thereof, hooks 13, 15 having, purely exemplarily, four tips or end sections 13a, 13b or 15a, 15b, respectively.

Unlike in the first and second embodiments of FIG. 1 to FIG. 6, the hooks extend from or are connected to a purely exemplary provided plate assembly 39 or from an arrangement differently designed. The hooks 13, 15 extend or protrude thereby in more than two (here: four) directions or compass directions, contributing to a good accessibility.

Unlike in the first and second embodiments of FIG. 1 to FIG. 6, the opening 3 is not one-piece, rather it subdivides in two openings or part-openings 3a and 3b. This subdivision takes place in the example of FIG. 7 through the middle area of the base section 1.

It is preferred that the part-openings 3a, 3b are of different sizes. In the example of FIG. 7, the part-opening 3b is large enough to receive or enclose the gating 207 shown in FIG. 3. That way, it is again ensured that the fluid bag rack 100 may stand stable despite the gating 207. Since the gating 207 may be in a middle (in longitudinal direction) of the scale, the bag rack arm 9 is not provided in the middle (in longitudinal direction).

At the same time, providing two part-openings 3a, 3b (or also more than just two part-openings) allows saving material and above all weight. This makes the fluid bag rack 100 comparatively lighter and therefore better to handle by the personnel having to place it regularly at head height. In addition, saving weight allows better weighing results: the fluid bag rack 100 is placed in the scale 200, thus, weighed as well. The lower its weight is, the lower is the weighed weight and thus the scale may work in a lower measuring range. Since scales may usually weigh in a more exact manner in a lower measuring range (i.e. with lower weights) than in a higher measuring range (i.e. with heavier weights), the low weight of the fluid bag rack 100 advantageously contributes not only to a better handling, but also to higher measurement accuracy when weighing.

In the exemplary embodiment of FIG. 7, the bag rack arm 9 is optionally not arranged in the middle (in longitudinal direction, i.e. from the front to the back, with respect to the drawing of FIG. 7).

Figure 8:
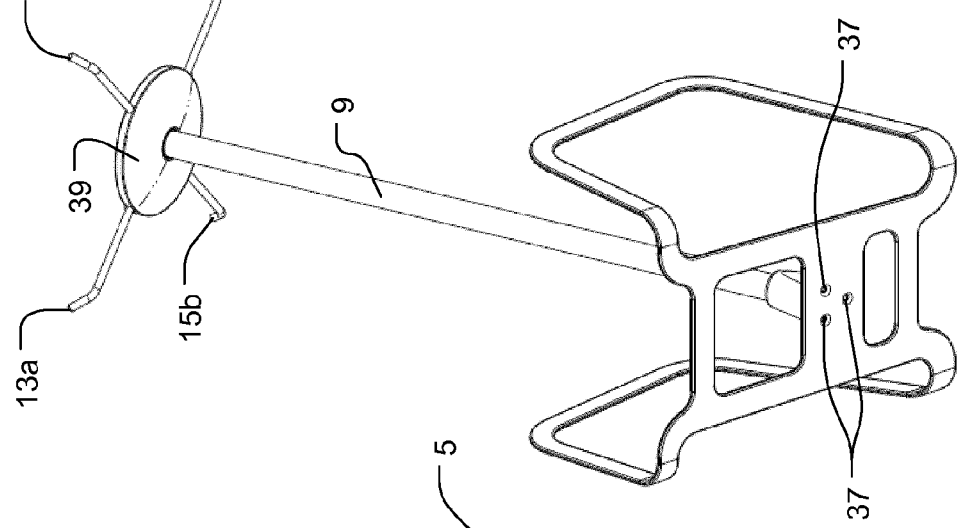
FIG. 8 shows the fluid bag rack of FIG. 7 in perspective view, diagonally from bottom rear.

FIG. 8 shows the fluid bag rack 100 of FIG. 7 in a perspective view diagonally from below and diagonally from the back.

Figure 9:
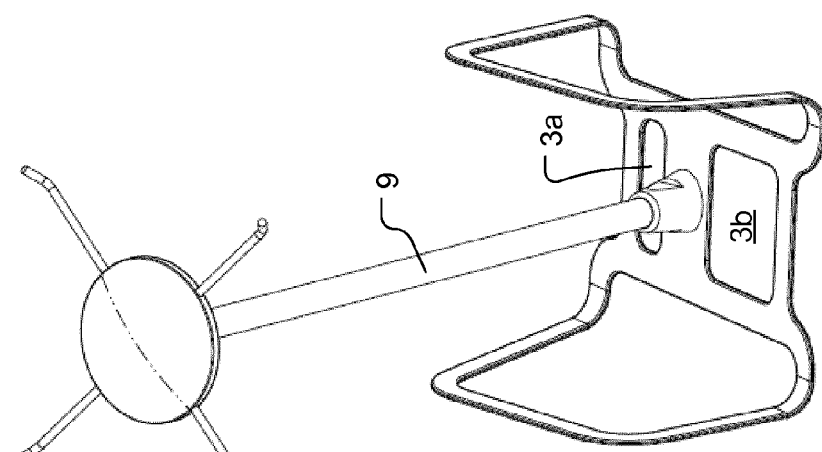
FIG. 9 shows the fluid bag rack of FIG. 7 and of FIG. 8 in perspective view, diagonally from rear top.

FIG. 9 shows the fluid bag rack 100 of FIG. 7 and of FIG. 8 in a perspective view diagonally from behind and diagonally from above.

LIST OF REFERENCE NUMERALS 100 fluid bag rack
1 base section
3 opening
3a, 3b (part)opening
5 support arm
5a lateral strut
5a' end section
5b lateral strut 5b' end section
5c cross strut
5d through space or through opening
7 support arm
7a lateral strut
7a' end section
7b lateral strut
7b' end section
7c cross strut
7d through space or through opening
9 bag rack arm
9a, 9b contacting or abutting edges or ends
11 bag rack arm
11a, 11b contacting or abutting edges or ends
13 hook
13a tip or end section
13b tip or end section
15 hook
15a tip or end section
15b tip or end section
17 connecting strut
19 holder
21 first metal strip
23 second metal strip
31 slot or groove or notch
33 slot or groove or notch
35 contacting or abutting area
37 screws
39 plate assembly
200 scale or scale pan
201 side surface
201a protrusion of the scale pan
203 side surface
203a protrusion of the scale pan
205 base area
207 gating
301 holding plate or sheet
303 holding plate or sheet
B width
B1 strip width
B2 strip width
H height
L length

The invention claimed is:

1. A fluid bag rack for hanging bags containing medical fluid, wherein the fluid bag rack comprises:
at least one base section;
at least two support arms which extend from the base section and which connect to the base section at sides of the base section lying opposite to each other, or extend as one-piece from the base section; and
at least one bag rack arm which extends from the base section,
wherein the at least one bag rack arm comprises one or more hooks configured to hang one or more fluid bags, and
wherein at least one of the support arms comprises two lateral struts, distanced from each other by an open slot.

2. The fluid bag rack according to claim 1, wherein the base section and the at least two support arms are manufactured as one-piece from one common strip of a first material, wherein the first material is metal.

3. The fluid bag rack according to claim 1, wherein the base section and the at least one bag rack arm are manufactured as one-piece from a common strip of a first material, wherein the first material is metal.

4. The fluid bag rack according to claim 1, wherein one of the support arms and the at least one bag rack arm are manufactured as one-piece from one common strip of a first material, wherein the first material is metal.

5. The fluid bag rack according to claim 1, wherein the bag rack arm has a cylindrical cross section and is connected to the base section.

6. The fluid bag rack according to claim 1, wherein at least two bag rack arms are connected to base section, sides of the base section lying opposite to each other, or extend as one-piece from the base section.

7. The fluid bag rack according to claim 1, wherein at least two bag rack arms are interconnected as one piece by a connecting section.

8. The fluid bag rack according to claim 7, wherein the base section, the bag rack arms and the connecting section are connected to each other to form a closed structure.

9. The fluid bag rack according to claim 1, wherein the base section comprises a flat section made of metal.

10. The fluid bag rack according to claim 9, wherein the flat section, comprises an opening in a middle part of the flat section.

11. The fluid bag rack according to claim 1, comprising at least a first material strip and a second material strip that comprises stainless steel, aluminum, standard steel or is varnished or powder-coated, or are plastic injection molded parts or plastic thermoformed parts.

12. The fluid bag rack according to claim 11, wherein the first material strip and the second material strip have a constant thickness between, 1 mm and 8 mm.

13. The fluid bag rack according to claim 1, wherein the one or more hooks are integral with the at least one bag rack arm.

14. The fluid bag rack according to claim 1, having at least one holding for releasable holding of fluid tube sections.

* * * * *